United States Patent
Nagamatsu et al.

(10) Patent No.: US 9,618,519 B2
(45) Date of Patent: Apr. 11, 2017

(54) METHOD FOR EVALUATING URINE SAMPLE, ANALYZER, AND ANALYSIS SYSTEM

(71) Applicant: ARKRAY, Inc., Kyoto (JP)

(72) Inventors: Ryuichiro Nagamatsu, Kyoto (JP); Shinya Nakajima, Kyoto (JP); Hideko Kosaka, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 14/817,429

(22) Filed: Aug. 4, 2015

(65) Prior Publication Data

US 2016/0041180 A1 Feb. 11, 2016

(30) Foreign Application Priority Data

Aug. 7, 2014 (JP) ................................. 2014-161900
Jul. 30, 2015 (JP) ................................. 2015-151193

(51) Int. Cl.
| | | |
|---|---|---|
| *G01N 33/68* | (2006.01) | |
| *G01N 35/00* | (2006.01) | |
| *G01N 33/493* | (2006.01) | |

(52) U.S. Cl.
CPC ......... *G01N 33/6827* (2013.01); *G01N 35/00* (2013.01); *G01N 33/493* (2013.01); *G01N 2800/347* (2013.01)

(58) Field of Classification Search
CPC ........... G01N 2800/347; G01N 33/493; G01N 33/68; G01N 33/6827; G01N 33/6839; G01N 35/00; G01N 21/78

USPC ...... 436/63, 86, 88, 164, 166, 169; 422/420, 422/68.1, 82.05, 82.09; 702/19
See application file for complete search history.

(56) References Cited

U.S. PATENT DOCUMENTS

| | | | |
|---|---|---|---|
| 6,673,630 B2 * | 1/2004 | Albarella ............ | G01N 33/521 422/424 |
| 2002/0086435 A1 * | 7/2002 | Fernandez Decastro ............ | G01N 33/526 436/164 |
| 2005/0214161 A1 | 9/2005 | Gupta | |
| 2010/0247377 A1 * | 9/2010 | Tsutsumida ......... | G01N 33/493 422/64 |
| 2013/0102082 A1 * | 4/2013 | Majima ................. | G01N 21/80 436/86 |

FOREIGN PATENT DOCUMENTS

JP 2009-204465 A 9/2009

OTHER PUBLICATIONS

Samarawickrama et al. HIV Medicine, vol. 13, 2012, pp. 526-532.*
Sakatsume, "Clinical utility of measurement of urinary protein/albumin," Journal of Analytical Bio-Science, 34: 106-110 (2011) (see English abstract).

(Continued)

*Primary Examiner* — Maureen Wallenhorst
(74) *Attorney, Agent, or Firm* — Morgan, Lewis & Bockius LLP

(57) ABSTRACT

A method for obtaining information about proteinuria and/or nephropathy from urine samples is provided for evaluating a urine sample that includes detecting proteins in the urine sample with two types of detection reagents that differ in reactivity to at least one urinary protein; and based on an indicator calculated using the results of the detection with the two types of detection reagents.

8 Claims, 5 Drawing Sheets

(56) References Cited

OTHER PUBLICATIONS

Shiba, "Disease diagnosis with electrophoretic analysis of urinary protein and comprehensive urinary proteome research," Journal of Analytical Bio-Science, 34: 111-119 (2011) (see English abstract).
Tsujikawa et al., "Evaluation of Novel Test Strip to Measure Albumin and Creatinine in Urine," Rinsho Byori, 53: 111-117 (2005) (see English abstract).
Extended European Search Report issued in corresponding European Patent Application No. 15180282.4 dated Oct. 23, 2015.
Ohisa et al., "A Comparison of Urinary Albumin-Total Protein Ratio to Phase-Contrast Microscopic Examination of Urine Sediment for Differentiating Glomerular and Nonglomerular Bleeding," American Journal of Kidney Diseases, 52: 235-241 (2008).

\* cited by examiner

METHOD FOR EVALUATING URINE SAMPLE, ANALYZER, AND ANALYSIS SYSTEM

BACKGROUND OF THE INVENTION

1. Field of the Invention

The present disclosure relates to a method for evaluating a urine sample, an analyzer, and an analysis system.

2. Description of Related Art

Various proteins are excreted in urine which include a great deal of biological information. Urine containing a relatively high concentration of proteins is called proteinuria. The type of proteinuria can give information about nephropathy. For example, if the amount of albumin in urine is larger than a reference value, the urine can be classified as glomerular proteinuria. If the amount of $\alpha$1-microglobulin or $\beta$2-microglobulin in urine is larger than a reference value, the urine can be classified as tubular proteinuria. See Minoru Sakatsume ("Clinical utility of measurement of urinary protein/albumin", Journal of Analytical Bio-Science, Vol. 34, No. 2, pp. 106-110 (2011)). Moreover, Kiyoko Shiba ("Disease diagnosis with electrophoretic analysis of urinary protein and comprehensive urinary proteome research", Journal of Analytical Bio-Science, Vol. 34, No. 2, pp. 111-119 (2011)) and JP 2009-204465 A1 disclose a method for diagnosing a renal disease state by detecting urinary proteins in a urine sample.

In clinical laboratory tests, a plurality of urine samples are measured by a sample analyzer. For example, a sample analyzer including a sample analysis tool with one or more types of test strips has generally been used (see Hitomi Tsujikawa et al., "Evaluation of novel test strip to measure albumin and creatinine in urine", Rinsho Byori, 53, pp. 111-117). The test strips may be, e.g., a "protein test strip (pad)" for detecting urinary proteins, an "albumin test strip (pad)" for detecting a trace amount of albumin in urine, and a "creatinine test strip (pad)" for detecting creatinine in urine.

SUMMARY OF THE INVENTION

The urinary protein analysis and the urinary proteome analysis of Kiyoko Shiba ("Disease diagnosis with electrophoretic analysis of urinary protein and comprehensive urinary proteome research", Journal of Analytical Bio-Science, Vol. 34, No. 2, pp. 111-119 (2011)) and JP 2009-204465 A1 have the advantage of obtaining important biological information. However, these analyses require that proteins present in urine be separated and fractionated individually. Therefore, performing the analyses of urine samples is complicated and costly.

Thus, in one or more embodiments, the present disclosure provides a method for obtaining information about proteinuria and/or nephropathy from urine samples more easily and at a lower cost.

In one or more embodiments, the present disclosure relates to a method for evaluating a urine sample that includes the following: detecting proteins in the urine sample with two types of detection reagents that differ in reactivity to at least one urinary protein; and evaluating the urine sample based on an indicator that is calculated using the results of the detection with the two types of detection reagents.

In one or more embodiments, the present disclosure relates to a method for evaluating a urine sample that includes the following: detecting proteins in the urine sample with two types of detection reagents that differ in their relative reactivities to a urinary protein a and a urinary protein b; and evaluating the urine sample based on an indicator that is calculated using the results of the detection with the two types of detection reagents. If the amount of the urinary protein a in the urine sample is larger than a reference value, the urine sample is classified as proteinuria A. If the amount of the urinary protein b in the urine sample is larger than a reference value, the urine sample is classified as proteinuria B.

In one or more embodiments, the present disclosure relates to a method for evaluating a urine sample that includes the following: evaluating the urine sample based on an indicator calculated using a P value and an A value, where the P value is determined using a protein detection reagent for detecting proteins in the urine sample, and the A value is determined using a detection reagent having a higher detection sensitivity to albumin than the protein detection reagent.

In one or more embodiments, the present disclosure relates to an analyzer including the following: a measurement portion configured to optically analyze coloration after a urine sample is brought into contact with two types of detection reagents that differ in reactivity to at least one urinary protein; a recording portion configured to record data for evaluating the urine sample; an operation portion configured to calculate an indicator from the results of the optical analysis of the two types of detection reagents, and configured to evaluate the urine sample based on the data for evaluating the urine sample; and an output portion configured to output data after the evaluation.

In one or more embodiments, the present disclosure relates to an analyzer including the following: a measurement portion configured to optically analyze coloration after a urine sample is brought into contact with two types of detection reagents that differ in their relative reactivities to a urinary protein a and a urinary protein b; a recording portion configured to record data for evaluating the urine sample; an operation portion configured to calculate an indicator from the results of the optical analysis of the two types of detection reagents, and configured to evaluate the urine sample based on the data for evaluating the urine sample; and an output portion configured to output data after the evaluation.

In one or more embodiments, the present disclosure relates to an analyzer including the following: a measurement portion configured to optically analyze coloration after a urine sample is brought into contact with a protein detection reagent for detecting protein in the urine sample, and coloration after the urine sample is brought into contact with a detection reagent having a higher detection sensitivity to albumin than the protein detection reagent; a recording portion configured to record data for evaluating the urine sample; an operation portion configured to calculate an indicator from the results of the optical analysis of the two types of detection reagents, and configured to evaluate the urine sample based on the data for evaluating the urine sample; and an output portion configured to output data after the evaluation.

In one or more embodiments, the present disclosure relates to an analysis system including an analysis tool and an analyzer that uses the analysis tool for an analysis. The analysis tool includes two types of detection reagents that differ in reactivity to at least one urinary protein or two types of detection reagents that differ in their relative reactivities to a urinary protein a and a urinary protein b. The analyzer includes the following: a measurement portion configured to optically analyze coloration after a urine sample is brought into contact with the two types of detection reagents; a recording portion configured to record data for evaluating the urine sample; an operation portion configured to calculate an indicator from the results of the optical analysis of the two types of detection reagents, and configured to evaluate the urine sample based on the data for evaluating the urine sample; and an output portion configured to output data after the evaluation.

In one or more embodiments, the present disclosure provides a method for obtaining information about proteinuria and/or nephropathy from a urine sample easily.

DETAILED DESCRIPTION OF THE INVENTION

In clinical laboratory tests, a urine sample is often measured by a sample analysis tool and a fully-automated or semiautomated sample analyzer. The sample analysis tool generally includes a "protein test strip (pad)" (also referred to as a "total protein test strip") for detecting urinary proteins. Moreover, the sample analysis tool may include an "albumin test strip (pad)" (also referred to as a "trace protein test strip") for detecting a trace amount of albumin (or a trace protein) in urine, and a "creatinine test strip (pad)" for detecting creatinine in urine. The output of the sample analyzer may be, e.g., the measured protein value that is corrected with the measured creatinine value (P/C value) and defined as either positive or negative, and the measured albumin value that is corrected with the measured creatinine value (A/C value) and defined as either positive or negative.

In general, the albumin test strip has a higher detection sensitivity to albumin than the protein test strip. Therefore, if the A/C value (i.e., the result of the albumin test strip) is negative, the P/C value (i.e., the result of the protein test strip) is also negative. Moreover, if the A/C value is positive, the P/C value is generally positive or negative. However, the present inventors studied a large number of urine samples and found that some of them showed that the P/C value was positive although the A/C value was negative. The present inventors further proceeded with the study and learned that the relative reactivities of a combination of some of the urinary proteins in renal proteinuria were different between the protein test strip and the albumin test strip.

Figure 6:
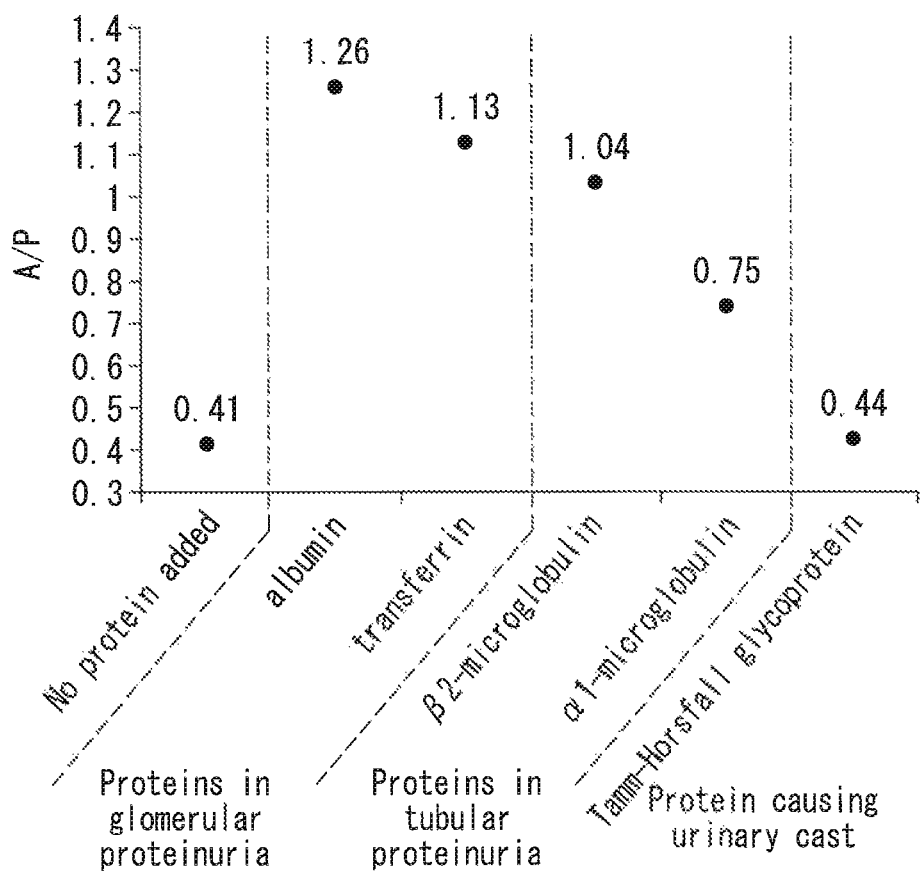
FIG. 6 is a graph showing an example of the relationship between urinary proteins and A/P values of proteinuria.

In one or more embodiments, the present disclosure is based on the findings that the A/P value or the P/A value calculated from the A value and the P value or the A/C value and the P/C value can be new indicators showing (i) the presence or absence of an abnormality in a urine sample, (ii) the presence or absence of a suspicion of pathological proteinuria, (iii) the presence or absence of a suspicion of tubular proteinuria, (iv) the presence or absence of a suspicion of glomerular proteinuria, or (v) any combination of (i) to (iv) in accordance with the value (see, e.g., FIG. 6). The P/C value and the A/C value are not merely calculated by dividing the P value (i.e., the measured value of the protein test strip) and the A value (i.e., the measured value of the albumin test strip) by the measured creatinine value C, respectively, but are also calculated based on a correction formula including those values. The correction formula can be appropriately determined by the reactivity of each reagent or the like.

[Urine Sample]

The "urine sample" of the present disclosure is urine derived from a living organism or a sample that is prepared from the urine derived from a living organism. In one or more embodiments, examples of the living organism include humans and mammals other than humans. In one or more embodiments, the humans may include healthy people, patients, and subjects of urinalysis or medical examination. The above preparation is not particularly limited, and may be performed by dilution or addition of a buffer.

[Urinary Protein]

The "urinary proteins" of the present disclosure are proteins contained in urine. In one or more embodiments, urine may contain proteins that are detected in proteinuria, proteins whose concentration is specifically increased in proteinuria, proteins that are distinctive in proteinuria, or a combination of these proteins. "Proteinuria" is generally classified into physiological proteinuria and pathological proteinuria. Pathological proteinuria is classified into prerenal proteinuria, renal proteinuria, and postrenal proteinuria. Renal proteinuria is further subclassified into glomerular proteinuria and tubular proteinuria. For example, if the amount of albumin or transferrin in urine is larger than a reference value, the urine is classified as glomerular proteinuria. If the amount of $\alpha 1$-microglobulin, $\beta 2$-microglobulin, retinol binding protein, lysozyme, or N-acetylglucosaminidase in urine is larger than a reference value, the urine is classified as tubular proteinuria. If the amount of Bence-Jones protein, hemoglobin, or myoglobin in urine is larger than a reference value, the urine is classified as prerenal proteinuria. If the amount of deviation enzyme such as phosphatase or secretory IgA in urine is larger than a reference value, the urine is classified as postrenal proteinuria. In general, the "urinary proteins in glomerular proteinuria" have a higher molecular weight than the "urinary proteins in tubular proteinuria".

[Detection Reagent]

The "detection reagent" of the present disclosure can detect a component in a urine sample and may be in any form. In one or more embodiments, the detection reagent may be arranged in a reagent layer of the analysis tool and prepared in the following manner. A water-absorbing porous material such as filter paper is impregnated with an aqueous solution of the detection reagent, dried, and optionally bonded with a water impermeable material that serves as a handle. Alternatively, the detection reagent may be in the form of a powder or a solid. In one or more other embodiments, the detection reagent may be dissolved in a liquid to form a liquid reagent.

In one or more embodiments, it is preferable that the detection reagent of the present disclosure, which is used for the detection of a protein, changes color with the concentration of the protein for ease of sample analysis. In one or more embodiments, the detection reagent exhibits a color transition when it comes into contact with a protein in a solution, thereby detecting the presence of the protein in the solution and/or measuring the concentration of the protein in the solution. Any material that has conventionally been known and/or that will be developed in the future can be used as the detection reagent. For example, materials disclosed in WO 2004/015423 etc. can be used. Examples of the detection reagent include an octahalosulfophthalein-type dye, an octahalophenolphthalein-type dye, and a combination of these dyes. More specifically, the detection reagent may be selected from the group consisting of tetrabromophenol blue, tetrachlorophenol blue, 4,5,6,7-tetrachloro-2',4',5',7'-tetraiodo-fluorescein disodium, 3',3",5,5"-tetraiodo-3,4,5,6-tetrabromophenolsulfophthalein, 3,3"-diiodo-5,5",3,4,5,6-hexabromophenolsulfophthalein, methyl yellow (4-dimethylaminoazobenzene), salts thereof, and combinations thereof.

[Detection with Detection Reagent]

In one or more embodiments, the "detection with a detection reagent" of the present disclosure includes "optically analyzing coloration after a urine sample is brought into contact with the detection reagent". In one or more embodiments, "bringing the urine sample into contact with the detection reagent" of the present disclosure may include the following: mixing the urine sample and a solution of the detection reagent; dipping a reagent piece (strip) that has a reagent pad (reagent layer) containing the detection reagent in a dry state into the urine sample; and dropping the urine sample onto the reagent pad containing the detection reagent in a dry state. However, the contact between the urine sample and the detection reagent is not limited to the above, and can be made in a manner that has conventionally been known and/or that will be developed in the future.

The "optical analysis" of the present disclosure is not particularly limited. In one or more embodiments, the optical analysis may be a spectroscopic analysis that uses a spectrometer or the like to measure transmitted light, reflected light, or scattered light of an object so that information about the object is obtained. The results of the optical analysis can provide, e.g., the absorbance, transmittance, or reflectance of the object at a desired wavelength. For example, the optical analysis may include detecting transmitted light, reflected light, or scattered light of the detection reagent in contact with the urine sample, and calculating a value that represents the optical characteristics such as absorbance, transmittance, or reflectance of the detection reagent from the detected light. The optical analysis is not limited to the above, and may also include the measurement using another optical method and/or spectroscopic method.

The "optical analysis of coloration after the urine sample is brought into contact with the detection reagent" of the present disclosure may differ depending on the contact between the urine sample and the detection reagent. For example, if the contact is made by mixing a liquid sample and a liquid reagent for detecting protein, the liquid mixture is optically analyzed. If the contact is made by dipping the reagent pad (reagent layer) containing the detection reagent in a dry state into the liquid sample or by dropping the liquid sample onto the reagent pad containing the detection reagent in a dry state, the reagent pad after the dipping or dropping is optically analyzed. However, the optical analysis is not limited to the above, and may be performed in any conventionally known manner. The "coloration" in the present specification may include color developed from a colorless state and color produced by the transition from another color.

[Indicator]

The "indicator" of the present disclosure is used to evaluate a urine sample. In one or more embodiments, the "indicator" of the present disclosure is calculated using the results of the detection of proteins in the urine sample with two types of detection reagents that differ in reactivity to at least one urinary protein. In one or more embodiments, the "indicator" of the present disclosure is calculated using the results of the detection of proteins in the urine sample with two types of detection reagents that differ in their relative reactivities to a urinary protein a and a urinary protein b. In one or more other embodiments, the "indicator" of the present disclosure is calculated using a P value that is determined using a protein detection reagent for detecting protein in the urine sample, and an A value that is determined using a detection reagent having a higher detection sensitivity to albumin than the protein detection reagent.

[Indicators: A/P Value and P/A Value]

In one or more non-limiting embodiments, the "indicator" of the present disclosure is the following A/P value or P/A value.

$$A/P \text{ value}=[A \text{ value}]/[P \text{ value}] \text{ or } [A/C \text{ value}]/[P/C \text{ value}]$$

$$P/A \text{ value}=[P \text{ value}]/[A \text{ value}] \text{ or } [P/C \text{ value}]/[A/C \text{ value}]$$

The P value is determined using the protein detection reagent for detecting protein in the urine sample. The P/C value is calculated by correcting the P value with the C value that is determined using a creatinine detection reagent for detecting creatinine in the urine sample. The A value is determined using the detection reagent having a higher detection sensitivity to albumin than the protein detection reagent. The A/C value is calculated by correcting the A value with the C value.

[Creatinine Correction]

The concentration of proteins in urine varies with the state of water metabolism at the time of urine collection. In general, it is preferable that the concentration of a protein or proteins is corrected with the value of creatinine in urine. Therefore, in one or more embodiments, the method for evaluating a urine sample of the present disclosure includes detecting creatinine in urine with a creatinine detection reagent for detecting creatinine in urine. For example, in the sample analysis tool or sample analyzer for a urine sample, urinary creatinine may be measured at the same time as the measurement of urinary proteins (components), and the measured value may be corrected with the creatinine value. In many cases, the creatinine correction uses a correction coefficient or a correction formula. However, the correction coefficient or the correction formula is appropriately determined by urinary proteins (components).

[Evaluation of Urine Sample]

In one or more embodiments, the "evaluation of a urine sample" of the present disclosure may be selected from the group consisting of (i) the presence or absence of an abnormality in the urine sample, (ii) the presence or absence of a suspicion of pathological proteinuria, (iii) the presence or absence of a suspicion of tubular proteinuria, (iv) the presence or absence of a suspicion of glomerular proteinuria, and (v) any combination of (i) to (iv). Therefore, in one or more embodiments, the "evaluation of a urine sample" may include the evaluation of nephropathy in accordance with proteinuria. Moreover, in one or more embodiments, the "evaluation of a urine sample" may include the evaluation of a urinary tract disorder other than the evaluation of nephropathy. In one or more embodiments, the "evaluation of a urine sample" of the present disclosure may be performed based on the data for evaluating the urine sample.

[Data for Evaluating Urine Sample]

The "data for evaluating the urine sample" of the present disclosure includes information about how to evaluate the urine sample based on the indicator. In one or more non-limiting embodiments, "the data for evaluating the urine sample" may include predetermined criteria (such as a range of the indicator and a threshold value) and contents of the evaluation in connection with the predetermined criteria. Moreover, in one or more embodiments, the "data for evaluating the urine sample" may include a calculation method of the indicator, e.g., a formula for calculating the indicator from the results of the optical analysis of the measured values obtained by the detection reagents. In one or more embodiments, using the samples of subjects whose disease states have been identified, indicators of the present disclosure are calculated and a quantitative analysis is performed with higher accuracy, so that the data for evaluating the urine sample can be created and updated by analyzing the indicators and the results of the quantitative analysis.

In one or more embodiments, the data for evaluating the urine sample may include data concerning the evaluation of the urine sample for each of the ranges (criteria) of the indicator (A/P value) (see the following Table 1 or 2). In this embodiment, the calculated A/P value and/or the evaluation in connection with this A/P value are output. The numerical values in Tables 1 and 2 are only examples and do not limit the present disclosure.

TABLE 1

| Criteria | Evaluation |
| --- | --- |
| A/P < 0.83 | No abnormality is found. |
| 0.83 ≤ A/P | An abnormality is found, and there is a suspicion of proteinuria. |

TABLE 2

| | Criteria | Evaluation |
| --- | --- | --- |
| First criterion | A/P < 0.83 | No abnormality is found. |
| Second criterion | 0.83 ≤ A/P < 0.88 | There is a suspicion of tubular proteinuria, and quantification of α1-microglobulin and β2-microglobulin is recommended. |
| Third criterion | 0.88 ≤ A/P < 0.91 | There is a suspicion of both tubular proteinuria and glomerular proteinuria, and quantification of albumin, transferrin, α1-microglobulin, and β2-microglobulin is recommended. |
| Fourth criterion | 0.91 ≤ A/P | There is a suspicion of glomerular proteinuria, and quantification of albumin and transferrin is recommended. |

In the example of Table 1, the indicator (A/P value) can be used to evaluate the presence or absence of an abnormality in the urine sample, i.e., whether there is a suspicion that the urine sample may be proteinuria. In the example of Table 2, the indicator (A/P value) can be used to evaluate the presence or absence of an abnormality in the urine sample, the presence or absence of a suspicion of tubular proteinuria, and the presence or absence of a suspicion of glomerular proteinuria.

Therefore, in one or more embodiments, the present disclosure can easily provide screening of proteinuria and/or nephropathy by the sample analyzer. Moreover, in one or more other embodiments, the present disclosure can easily provide screening of proteinuria and/or nephropathy by the sample analysis method using a test strip such as a sample analysis tool.

[Method for Evaluating Urine Sample: First Aspect]

In an aspect, the present disclosure relates to a method for evaluating a urine sample that includes the following: detecting proteins in the urine sample with two types of detection reagents that differ in reactivity to at least one urinary protein; and evaluating the urine sample based on an indicator that is calculated using the results of the detection with the two types of detection reagents.

In one or more embodiments, the meaning of "one urinary protein" in the evaluation method of the first aspect includes "at least one urinary protein", and the "two types of detection reagents that differ in reactivity to at least one urinary protein" may also differ in reactivity to a plurality of urinary proteins.

In one or more non-limiting embodiments, the "at least one urinary protein" in the evaluation method of the first aspect is albumin. In one or more embodiments, "two types of detection reagents that differ in reactivity to albumin" may be a combination of a protein detection reagent for detecting protein in the urine sample and a detection reagent having a higher detection sensitivity to albumin than the protein detection reagent. In one or more embodiments, the "protein detection reagent for detecting protein in the urine sample" of the present disclosure includes a protein detection reagent for detecting total protein in the urine sample. In one or more embodiments, the "protein detection reagent for detecting total protein in the urine sample" includes a protein detection reagent for detecting a plurality of urinary proteins in the urine sample, or a protein detection reagent for detecting more types of urinary proteins in the urine sample.

The protein detection reagent for detecting protein in the urine sample differs generally from the detection reagent having a higher detection sensitivity to albumin than the protein detection reagent in the following points. In one or more embodiments, the former selects the conditions (pH, reagent, additive, etc.) to detect more types of proteins, and the latter selects the conditions (pH, reagent, additive, etc.) suitable to detect albumin or a specific trace protein. As described above, the sample analysis tool for a urine sample generally includes a detection reagent for detecting protein (total protein) (i.e., a protein test strip) and a detection reagent for detecting albumin or a trace protein (i.e., an albumin test strip). In many cases, the protein test strip generally uses a protein error method. The albumin test strip differs generally from the protein test strip in formulation, and has a high detection sensitivity to albumin. However, the "two types of detection reagents that differ in reactivity to at least one urinary protein" of the present disclosure are not limited to the above, and three or more types of detection reagents may be used in this aspect.

In one or more embodiments, the "indicator" in the evaluation method of the first aspect is calculated using the results of the detection of proteins in the urine sample with two types of detection reagents that differ in reactivity to at least one urinary protein. In one or more non-limiting embodiments, the indicator may be a ratio of two measured values (including the creatinine correction or the like) obtained by the two types of detection reagents that differ in reactivity to at least one urinary protein. In one or more further embodiments, the indicator may be the A/P value or P/A value.

[Method for Evaluating Urine Sample: Second Aspect]

In another aspect, the present disclosure relates to a method for evaluating a urine sample that includes the following: detecting proteins in the urine sample with two types of detection reagents that differ in their relative reactivities to a urinary protein a and a urinary protein b; and evaluating the urine sample based on an indicator that is calculated using the results of the detection with the two types of detection reagents. If the amount of the urinary protein a in the urine sample is larger than a reference value, the urine sample is classified as proteinuria A. If the amount of the urinary protein b in the urine sample is larger than a reference value, the urine sample is classified as proteinuria B. The urinary proteins a, b may be used as standards indicating, e.g., a suspicion of nephropathy.

In one or more non-limiting embodiments, the combination of the proteinuria A and the proteinuria B may be a combination of glomerular proteinuria and tubular proteinuria. In this case, examples of the urinary protein a include albumin and transferrin, and examples of the urinary protein b include α1-microglobulin, β2-microglobulin, retinol binding protein, lysozyme, and N-acetylglucosaminidase.

In one or more embodiments, the "relative reactivity" of this aspect may be represented by [a]/[b] or [b]/[a], where [a] and [b] are the measured values when the urinary protein a and the urinary protein b are separately detected with the same detection reagent, respectively. The "two types of detection reagents that differ in their relative reactivities" mean that [a]/[b] or [b]/[a] is different between the two types of detection reagents. In one or more embodiments, the evaluation method of the present disclosure is based on the findings that focusing attention on the difference in relative reactivities of two types of urinary proteins can lead to a suspicion that the urine sample is a particular type of proteinuria even by a simple detection/measurement method using a test strip or the like.

The "two types of detection reagents that differ in their relative reactivities" in the evaluation method of the second aspect are not particularly limited. In one or more embodiments, the two types of detection reagents may be a combination of the protein detection reagent for detecting protein (total protein) in the urine sample and the detection reagent having a higher detection sensitivity to albumin than the protein detection reagent, as described above. The reactivity of albumin (i.e., the urinary protein in glomerular proteinuria) is generally higher with the "detection reagent having a higher detection sensitivity to albumin than the protein detection reagent" than with the "protein detection reagent for detecting protein". The reactivity of α1-microglobulin or β2-microglobulin (i.e., the urinary protein in tubular proteinuria) is generally higher with the "protein detection reagent for detecting protein" than with the "detection reagent having a higher detection sensitivity to albumin than the protein detection reagent". Therefore, the reactivity of α1-microglobulin or β2-microglobulin relative to albumin is different between the protein detection reagent for detecting protein in the urine sample and the detection reagent having a higher detection sensitivity to albumin than the protein detection reagent. However, the "two types of detection reagents that differ in their relative reactivities" of the present disclosure are not limited to the above.

In one or more embodiments, the "indicator" in the evaluation method of the second aspect is calculated using the results of the detection of proteins in the urine sample with two types of detection reagents that differ in their relative reactivities to a urinary protein a and a urinary protein b. In one or more non-limiting embodiments, the indicator may be a ratio of two measured values (including the creatinine correction or the like) obtained by the two types of detection reagents that differ in their relative reactivities to the urinary protein a and the urinary protein b. In one or more further embodiments, the indicator may be the A/P value or P/A value.

[Method for Evaluating Urine Sample: Third Aspect]

In another aspect, the present disclosure relates to a method for evaluating a urine sample that includes the following: evaluating the urine sample based on an indicator calculated using a P value and an A value, where the P value is determined using a protein detection reagent for detecting protein (total protein) in the urine sample, and the A value is determined using a detection reagent having a higher detection sensitivity to albumin than the protein detection reagent. In one or more non-limiting embodiments, the indicator may be a ratio of the P value (including the creatinine correction or the like) determined using the protein detection reagent for detecting protein in the urine sample and the A value (including the creatinine correction or the like) determined using the detection reagent having a higher detection sensitivity to albumin than the protein detection reagent. In one or more further embodiments, the indicator may be the A/P value or P/A value.

[Analysis Tool]

In the evaluation method of the present disclosure, a urine sample may be brought into contact with the detection reagent (and a creatinine detection reagent as needed) in the reagent layer (test pad) on the test strip, as described above. Therefore, in another aspect, the present disclosure relates to an analysis tool that includes a substrate and at least two reagent layers containing detection reagents on the substrate. In one or more embodiments, the substrate may be made of a water impermeable material and have a portion that serves as a handle. The two reagent layers may contain different detection reagents. The analysis tool of the present disclosure may include a reagent layer containing a detection reagent that can be used for correction such as a creatinine detection reagent. The analysis tool of the present disclosure may include a reagent layer other than the reagent layers containing the detection reagents and the reagent layer containing the detection reagent that can be used for correction such as a creatinine detection reagent. The number of the reagent layers is not particularly limited. The analysis tool of the present disclosure can be used for analysis in a conventionally known optical analyzer, and also be used for the evaluation method by the analyzer of the present disclosure, as will be described later.

Figure 1A:
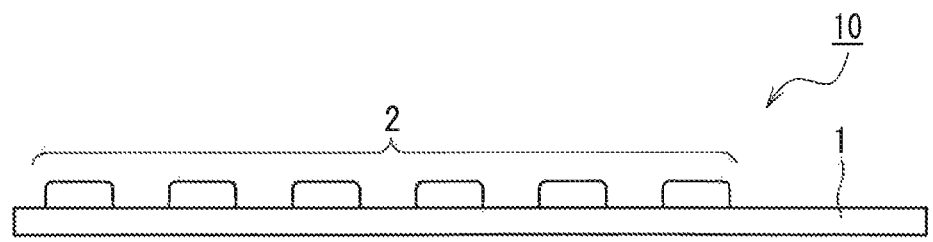
FIGS. 1A and 1B respectively show a side view and a top view of an analysis tool 10 of an embodiment of the invention.
Figure 1B:
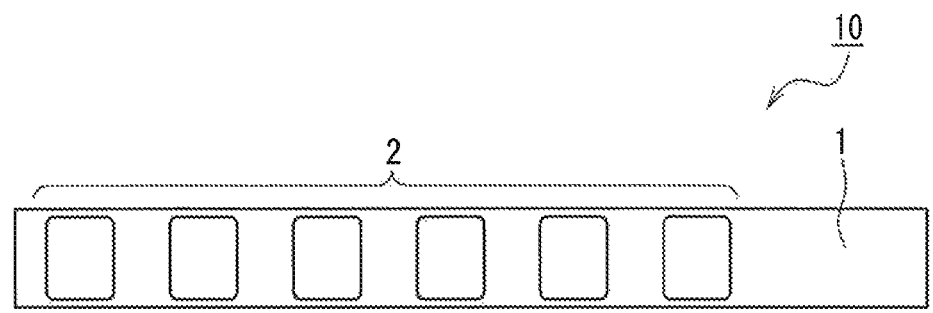

FIGS. 1A and 1B show an example of the analysis tool of the present disclosure. FIG. 1A is a side view and FIG. 1B is a top view. In FIGS. 1A and 1B, the same components are denoted by the same reference numerals. The sample analysis tool 10 includes a strip substrate 1 and six reagent layers (test pads) 2 formed on the substrate 1. The material of the substrate is not particularly limited, and may be, e.g., a resin, a metal, or glass. The color of the substrate is not particularly limited, and may be any of white, gray, black, chromatic color, and transparent color. The size of the substrate is not particularly limited, and may be appropriately determined by test items, the specification of the analyzer to be used, or the like. For example, the substrate is 50 to 150 mm in length, 2 to 10 mm in width, and 0.1 to 1.0 mm in thickness. The reagent layers 2 are formed by bonding pads onto the substrate 1. The pads are impregnated with predetermined reagents corresponding to the test items. The material of the pads may be, e.g., filter paper, glass fiber filter paper, knitted fabric, woven fabric, nonwoven fabric, membrane filter, or porous resin sheet. The shape of each of the reagent layers 2 (pads) is not particularly limited, and may be, e.g., square, rectangular, circular, or elliptical. The size of each of the reagent layers 2 (pads) is not particularly limited, and may be, e.g., 2 to 10 mm in length and width and 0.05 to 1.0 mm in thickness if the shape is a square. The number of the reagent layers 2 may be increased or decreased in accordance with the test items. The six reagent layers 2 are arranged in series at a constant pitch. The pitch is not particularly limited, and may be, e.g., 1.0 to 100 mm. In the sample analysis tool, no reagent layer 2 is provided on one end of the substrate 1 (i.e., the right end portion in FIGS. 1A and 1B), thereby leaving a space in this portion. Thus, the substrate 1 can be handled by holding this portion (holding portion) with the fingertips.

[Analyzer: First Aspect]

In another aspect, the present disclosure relates to an analyzer capable of performing the evaluation method of the present disclosure (also referred as an "analyzer of the present disclosure" in the following). In the first aspect, the analyzer of the present disclosure includes the following: a measurement portion configured to optically analyze coloration after a urine sample is brought into contact with two types of detection reagents that differ in reactivity to at least one urinary protein; a recording portion configured to record data for evaluating the urine sample; an operation portion configured to calculate an indicator from the results of the optical analysis of the two types of detection reagents, and configured to evaluate the urine sample based on the data for evaluating the urine sample; and an output portion configured to output data after the evaluation. The "two types of detection reagents that differ in reactivity to at least one urinary protein", the "indicator", and the "data for evaluating the urine sample" in the analyzer of the first aspect may be those described above, respectively.

[Analyzer: Second Aspect]

In the second aspect, the analyzer of the present disclosure includes the following: a measurement portion configured to optically analyze coloration after a urine sample is brought into contact with two types of detection reagents that differ in their relative reactivities to a urinary protein a and a urinary protein b; a recording portion configured to record data for evaluating the urine sample; an operation portion configured to calculate an indicator from the results of the optical analysis of the two types of detection reagents, and configured to evaluate the urine sample based on the data for evaluating the urine sample; and an output portion configured to output data after the evaluation. The "two types of detection reagents that differ in their relative reactivities to a urinary protein a and a urinary protein b", the "indicator", and the "data for evaluating the urine sample" in the analyzer of the second aspect may be those described above, respectively.

[Analyzer: Third Aspect]

In the third aspect, the analyzer of the present disclosure includes the following: a measurement portion configured to optically analyze coloration after a urine sample is brought into contact with a protein detection reagent for detecting protein in the urine sample, and coloration after the urine sample is brought into contact with a detection reagent having a higher detection sensitivity to albumin than the protein detection reagent; a recording portion configured to record data for evaluating the urine sample; an operation portion configured to calculate an indicator from the results of the optical analysis of the two types of detection reagents, and configured to evaluate the urine sample based on the data for evaluating the urine sample; and an output portion configured to output data after the evaluation. The two types of "detection reagents", the "indicator", and the "data for evaluating the urine sample" may be those described above, respectively.

In the analyzer of the present disclosure, the measurement portion for optically analyzing the detection reagents may perform either an optical analysis of a liquid or an optical analysis of the reagent layers of the analysis tool. Therefore, in one or more embodiments, the analyzer of the present disclosure uses the analysis tool of the present disclosure to perform the evaluation method of the present disclosure.

Figure 2:
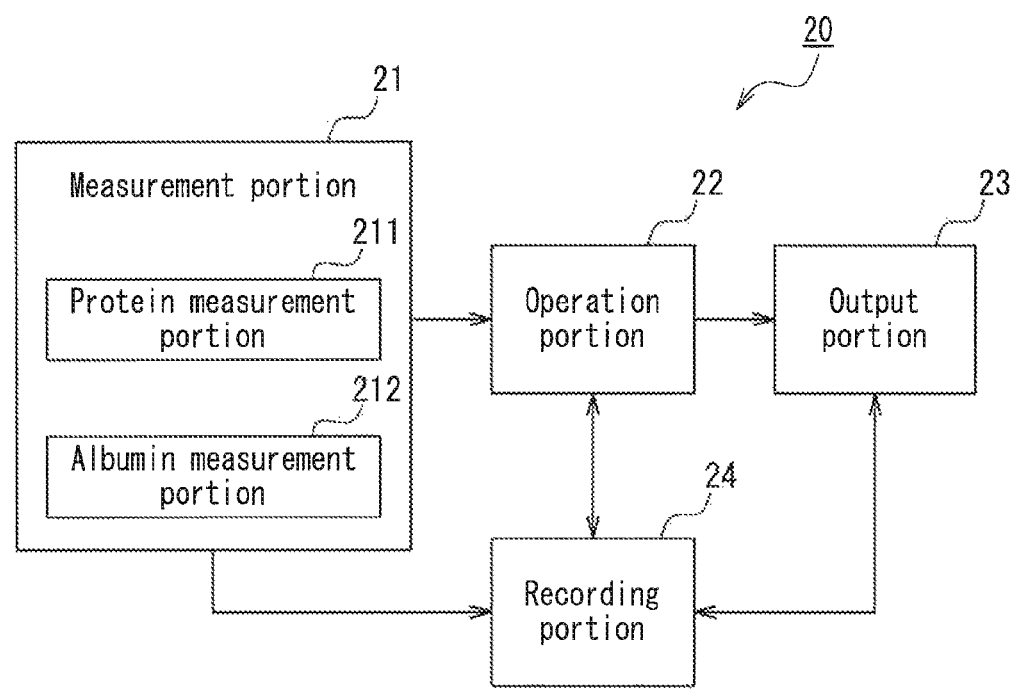
FIG. 2 is a functional block diagram showing a configuration example of an analyzer of an embodiment of the invention.

FIG. 2 is a functional block diagram showing a configuration example of an analyzer of an embodiment of the present disclosure. An analyzer 20 of FIG. 2 is an apparatus for evaluating a urine sample with the use of a detection reagent for detecting protein (total protein) and a detection reagent for detecting albumin or a trace protein (also referred to as "albumin" in the following). The analyzer 20 includes a measurement portion 21, an operation portion 22, an output portion 23, and a recording portion 24. The measurement portion 21 includes a protein measurement portion 211 and a trace albumin measurement portion 212. The results of the detection (optical analysis) of the detection reagents in the measurement portion 21 may be stored in the recording portion 24. The operation portion 22 performs the evaluation in accordance with the results of the optical analysis of the detection reagents in the measurement portion 21 and the data for evaluating the urine sample stored in the recording portion 24. The data for evaluating the urine sample may be created previously and stored in the recording portion 24. The results of the evaluation are stored in the recording portion 24 and/or output to the output portion 23. The output portion 23 may be, e.g., a display, a printer for printing, or a transmitter for transmitting data to the outside.

(Measurement Portion)

In the example of FIG. 2, the measurement portion 211 of the detection reagent for detecting protein and the measurement portion 212 of the detection reagent for detecting albumin constitute one measurement portion 21. In this case, the measurement portion 21 detects, e.g., transmitted light, reflected light, or scattered light of each of the reagent layers 2 of the analysis tool shown in FIGS. 1A and 1B to measure absorbance, reflectance, or transmittance. Although not shown in FIG. 2, the measurement portion 21 may include a measurement portion for detecting creatinine.

(Operation Portion)

The data for evaluating the urine sample used in the operation portion 22, and the evaluation method using the data for evaluating the urine sample in the operation portion 22 can be as described above.

In the analyzer 20 of FIG. 2, the measurement portion 211, the measurement portion 212, the operation portion 22, the output portion 23, and the recording portion 24 may be independent of one another and connected together, or all or part of these components may be integrally formed. The operation portion 22 can be achieved by a computer included in the analyzer 20. For example, a processor of the analyzer 20 executes a predetermined program, so that the function of the operation portion 22 can be performed. The recording portion 24 can be achieved by a recording medium such as a memory included in the analyzer 20 or a storage that can be accessed by the analyzer 20.

(Operation Example)

Figure 3:
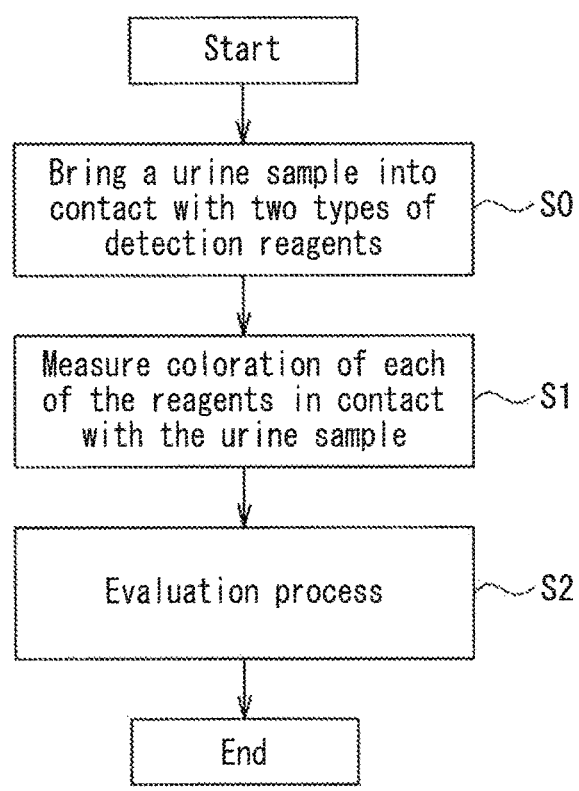
FIG. 3 is a flow chart showing an example of an operation of an analyzer of an embodiment of the invention.

FIG. 3 is a flow chart showing an operation example of the analyzer 20 shown in FIG. 2 (which is simply referred to as an analyzer in the following). In the example of FIG. 3, first, the processor of the analyzer controls the measurement portion 21 to bring a urine sample into contact with two types of detection reagents (S0). The measurement portion 21 measures coloration of each of the detection reagents in contact with the urine sample by optical analysis (S1). For example, the measurement portion 21 can make the contact between the urine sample and the detection reagents by dropping the urine sample onto the reagent layers containing the detection reagents of the analysis tool shown in FIGS. 1A and 1B. In this case, the measurement portion 21 measures absorbance, reflectance, or transmittance of the reagent layers, and thus can optically analyze the coloration of each of the detection reagents in contact with the urine sample. The results of the optical analysis (e.g., absorbance) by the measurement portion 21 are sent to the operation portion 22.

By using the results of the optical analysis of the detection reagents measured in S1 and the data for evaluating the urine sample stored in the recording portion 24, the operation portion 22 performs the evaluation process of the concentration of proteins in the urine sample (S2). Specifically, the operation portion 22 uses the data for evaluating the urine sample and calculates the indicator from the results of the optical analysis of the detection reagents measured in S1. The results of the evaluation produced by the operation portion 22 may either be the above indicator or the evaluation based on the indicator and the data for evaluating the urine sample. For example, the operation portion 22 produces the following as the results of the evaluation: the indicator itself; the presence or absence of an abnormality in the urine sample; the presence or absence of a suspicion of tubular proteinuria; the presence or absence of a suspicion of glomerular proteinuria; and the suggestion of a thorough examination. The output portion 23 outputs the results of the evaluation produced by the operation portion 22. The results of the evaluation may be output by, e.g., a display included in the analyzer, a printer, voice output from a speaker, data transmission through a network, or any combination of these options.

Figure 4:
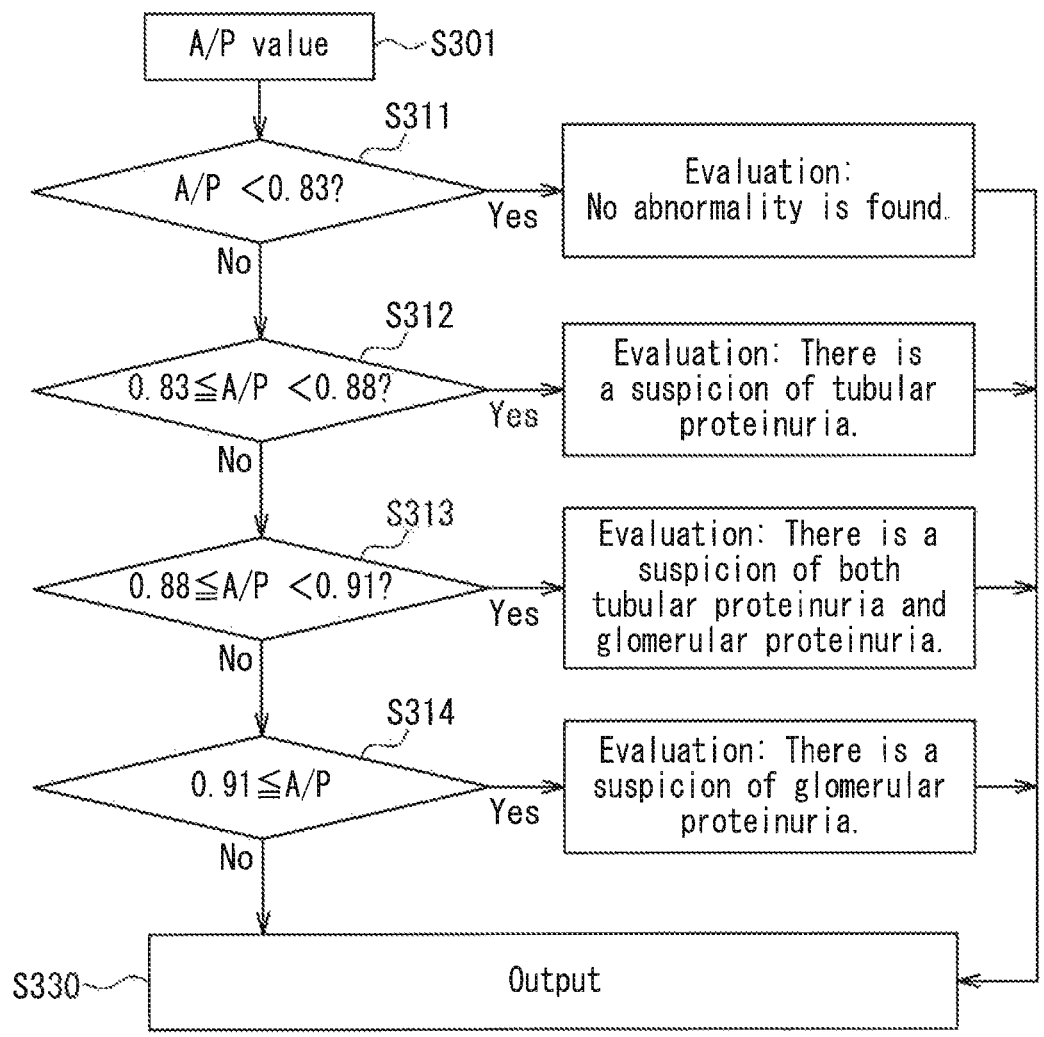
FIG. 4 is a flow chart showing another example of an operation of an analyzer of an embodiment of the invention.

FIG. 4 is a flow chart showing an operation example of the operation portion 22 in S2 of FIG. 3. The operation portion 22 calculates an A/P value of the detection reagents (S301). Then, the operation portion 22 selects the criteria and evaluation to be applied in accordance with the A/P value from the data for evaluating the urine sample stored in the recording portion 24 (S311 to S314). The following table 3 associates the contents of the evaluation with the ranges (criteria) of the A/P value.

TABLE 3

| | Criteria | Evaluation |
|---|---|---|
| First criterion | A/P < 0.83 | No abnormality is found. |
| Second criterion | 0.83 ≤ A/P < 0.88 | There is a suspicion of tubular proteinuria, and quantification of α1-microglobulin and β2-microglobulin is recommended. |
| Third criterion | 0.88 ≤ A/P < 0.91 | There is a suspicion of both tubular proteinuria and glomerular proteinuria, and quantification of albumin, transferrin, α1-microglobulin, and β2-microglobulin is recommended. |
| Fourth criterion | 0.91 ≤ A/P | There is a suspicion of glomerular proteinuria, and quantification of albumin and transferrin is recommended. |

For example, the operation portion 22 compares the first criterion of the data for evaluating the urine sample with the A/P value. If the A/P value is less than 0.83 ("Yes" in S311), the operation portion 22 extracts data indicating the content of the evaluation that "no abnormality is found", and outputs the data as the results of the evaluation (S330). If the A/P value is not less than 0.83 ("No" in S311), the operation portion 22 compares the second criterion of the data for evaluating the urine sample with the A/P value. Then, if the A/P value is not less than 0.83 and less than 0.88 ("Yes" in S312), the operation portion 22 extracts data indicating the content of the evaluation that "there is a suspicion of tubular proteinuria, and quantification of α1-microglobulin and β2-microglobulin is recommended", and outputs the data as the results of the evaluation (S330). If the A/P value is not less than 0.88 ("No" in S312), the operation portion 22 compares the third criterion of the data for evaluating the urine sample with the A/P value. Then, if the A/P value is not less than 0.88 and less than 0.91 ("Yes" in S313), the operation portion 22 extracts data indicating the content of the evaluation that "there is a suspicion of both tubular proteinuria and glomerular proteinuria, and quantification of albumin, transferrin, α1-microglobulin, and β2-microglobulin is recommended", and outputs the data as the results of the evaluation (S330). If the A/P value is not less than 0.91 ("No" in S313), the operation portion 22 compares the fourth criterion of the data for evaluating the urine sample with the A/P value. Then, if the A/P value is not less than 0.91 ("Yes" in S314), the operation portion 22 extracts data indicating the content of the evaluation that "there is a suspicion of glomerular proteinuria, and quantification of albumin and transferrin is recommended", and outputs the data as the results of the evaluation (S330). If it is "No" in S314, the operation portion 22 outputs "no evaluation" as the results of the evaluation (S330). The operation of the analyzer of the present disclosure is not limited to the example shown in FIGS. 3 and 4.

The present disclosure also includes a program that allows a computer to execute processes and output the evaluation of a urine sample. The processes include the following: acquiring results of an optical analysis of a detection reagent; accessing a recording portion in which data for evaluating the urine sample is previously stored, and evaluating the urine sample by selecting an evaluation method or evaluation criteria based on the results of the optical analysis of the detection reagent; and outputting the results of the evaluation. The present disclosure also includes a non-transitory recording medium that stores the program, and an analyzer in which the program is installed.

For example, one of the embodiments of the present disclosure is a program for evaluating a urine sample, and the program allows a computer to execute processes for evaluating a urine sample. The processes include the following: inputting results of an optical analysis of coloration after the urine sample is brought into contact with a detection reagent; and evaluating the urine sample based on the results of the optical analysis and data for evaluating the urine sample.

Moreover, one of the embodiments of the present disclosure is a program for controlling an analyzer, and the program allows the analyzer to execute the following processes: performing an optical analysis of coloration in a measurement portion after a urine sample is brought into contact with a detection reagent; evaluating the urine sample based on the results of the optical analysis and data for evaluating the urine sample; and outputting data after the evaluation. The data for evaluating the urine sample includes information that represents the evaluation criteria based on the indicator calculated from the results of the optical analysis.

(Specific Example of Analyzer)

Figure 5:
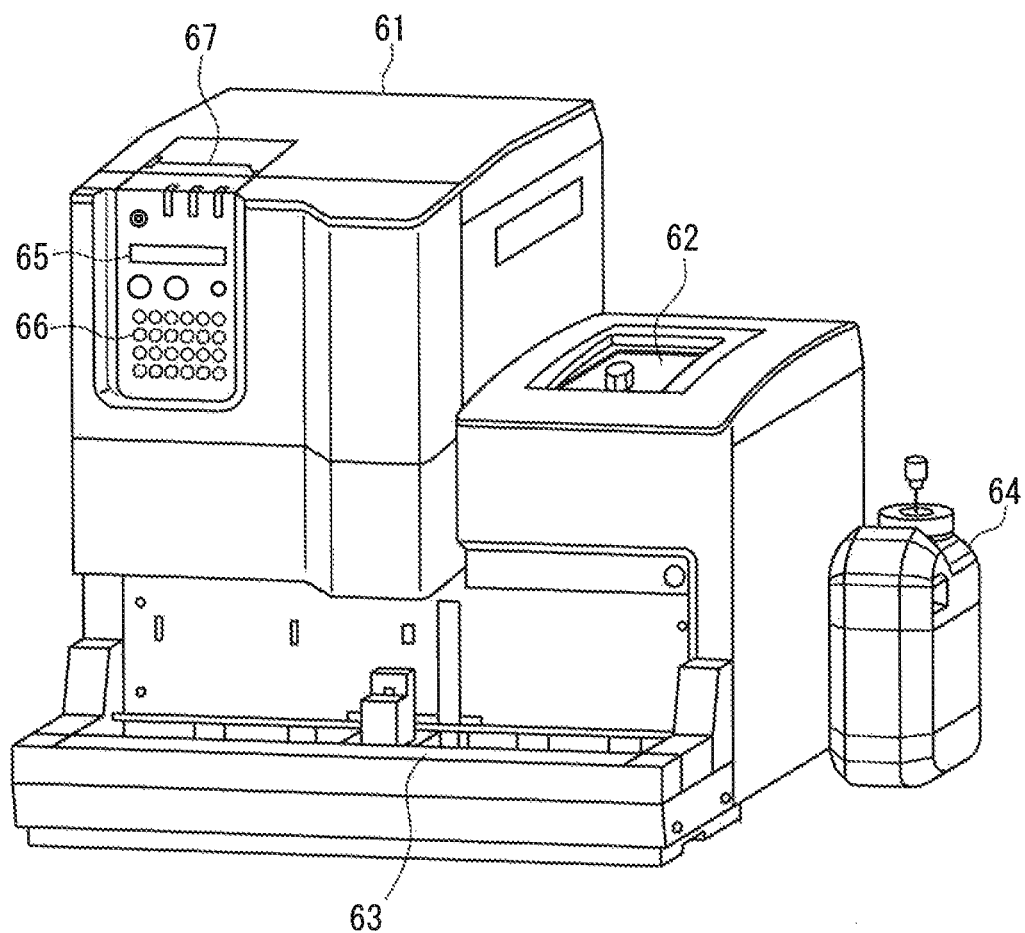
FIG. 5 is an external perspective view of a fully-automated urine chemistry analyzer using a urine analyzer of an embodiment of the invention.

FIG. 5 is an external perspective view of a fully-automated urine chemistry analyzer employing a urine analyzer that is a specific example of the analyzer 20. The fully-automated urine chemistry analyzer of FIG. 5 includes a main body 61, a test strip feeder 62, a sample feeder 63, and a bottle unit 64. The main body 61 includes a display 65, an operating portion 66, and a printer 67.

The main body 61 includes a movable nozzle, through which urine is drawn from a container of a urine sample that is placed in the sample feeder 63, and then the urine is dropped onto a plurality of reagent pads (i.e., an example of the reagent layers) arranged on a test strip (i.e., an example of the analysis tool) that has been transferred to a predetermined position inside the main body 61.

When the urine is dropped onto the reagent pads, the color or the like is measured by an optical system (corresponding to the measurement portion) located in the main body 61. Based on the results of the measurement, the protein detection reagents are evaluated in the operation portion, and the results of the evaluation are printed by the printer 67 and/or displayed on the display 65.

Although not shown in FIG. 5, the fully-automated urine chemistry analyzer may include a CPU, a memory (including, e.g., ROM (read only memory), RAM (random access memory), and HD (hard disk)), a motor driver, and a valve driver. The CPU is operated in accordance with the program stored in the memory. The memory stores the data for evaluating the urine sample. The CPU controls the motor driver and the valve driver. The motor driver is controlled by the CPU to drive a plurality of pumps for suction through the nozzle and washing. The valve driver is controlled by the CPU to drive a plurality of valves for suction through the nozzle and washing. The display, control, and input operations may be performed by an external apparatus (e.g., PC) connected to the main body 61, instead of providing the display 65 and the operating portion 66 in the main body 61. The results of the evaluation may be output not only to the display 65 or the printer 67 in the main body 61, but also to a display or the like of an external apparatus.

As described above, the analyzer may include the following: a means for placing protein detection reagents; a means for placing a urine sample; a means for bringing the urine sample into contact with the reagents; a means for measuring the colors of the reagents in contact with the urine sample by reflection, absorption, or the like; a means for analyzing the results of the measurement; and a means for controlling these operations. The analyzer is not limited to the above example.

[Analysis System]

In another aspect, the present disclosure relates to an analysis system including the analyzer of the present disclosure and the analysis tool used for the analysis method of the present disclosure. In one or more embodiments, the analysis system of this aspect includes an analysis tool and an analyzer that uses the analysis tool for an analysis. The analysis tool includes two types of detection reagents that differ in reactivity to at least one urinary protein or two types of detection reagents that differ in their relative reactivities to a urinary protein a and a urinary protein b. The analyzer includes the following: a measurement portion configured to optically analyze coloration after a urine sample is brought into contact with the two types of detection reagents; a recording portion configured to record data for evaluating the urine sample; an operation portion configured to calculate an indicator from the results of the optical analysis of the two types of detection reagents, and configured to evaluate the urine sample based on the data for evaluating the urine sample; and an output portion configured to output data after the evaluation. In one or more embodiments, the two types of detection reagents may be those described above. For example, the two types of detection reagents may be a combination of a protein detection reagent for detecting protein in the urine sample and a detection reagent having a higher detection sensitivity to albumin than the protein detection reagent. In one or more embodiments, the analysis tool and the analyzer in the analysis system of the present disclosure may be those described above.

The present disclosure may relate to one or more embodiments below.

[1] A method for evaluating a urine sample including:
detecting proteins in the urine sample with two types of detection reagents that differ in reactivity to at least one urinary protein; and
evaluating the urine sample based on an indicator that is calculated using the results of the detection with the two types of detection reagents.

[2] The method according to [1], wherein the at least one urinary protein is albumin.

[3] The method according to [1] or [2], wherein a combination of the two types of detection reagents is a combination of a protein detection reagent for detecting protein in the urine sample and a detection reagent having a higher detection sensitivity to albumin than the protein detection reagent.

[4] A method for evaluating a urine sample including:
detecting proteins in the urine sample with two types of detection reagents that differ in their relative reactivities to a urinary protein a and a urinary protein b; and
evaluating the urine sample based on an indicator that is calculated using the results of the detection with the two types of detection reagents,
wherein if an amount of the urinary protein a in the urine sample is larger than a reference value, the urine sample is classified as proteinuria A, and if an amount of the urinary protein b in the urine sample is larger than a reference value, the urine sample is classified as proteinuria B.

[5] The method according to [4], wherein a combination of the proteinuria A and the proteinuria B is a combination of glomerular proteinuria and tubular proteinuria.

[6] The method according to [4] or [5], wherein a combination of the two types of detection reagents is a combination of a protein detection reagent for detecting protein in the urine sample and a detection reagent having a higher detection sensitivity to albumin than the protein detection reagent.

[7] A method for evaluating a urine sample including:
evaluating the urine sample based on an indicator calculated using a P value and an A value, where the P value is determined using a protein detection reagent for detecting protein in the urine sample, and the A value is determined using a detection reagent having a higher detection sensitivity to albumin than the protein detection reagent.

[8] The method according to any one of [1] to [7], wherein the indicator has the following A/P value or P/A value:

$$A/P \text{ value} = [A \text{ value}]/[P \text{ value}] \text{ or } [A/C \text{ value}]/[P/C \text{ value}];$$

$$P/A \text{ value} = [P \text{ value}]/[A \text{ value}] \text{ or } [P/C \text{ value}]/[A/C \text{ value}],$$

where the P value is determined using the protein detection reagent for detecting protein in the urine sample, the P/C value is calculated by correcting the P value with a C value that is determined using a creatinine detection reagent for detecting creatinine in the urine sample, the A value is determined using the detection reagent having a higher detection sensitivity to albumin than the protein detection reagent, and the A/C value is calculated by correcting the A value with the C value.

[9] The method according to [8], wherein the A/C value is used as the indicator.

[10] The method according to any one of [1] to [9], wherein the evaluation of the urine sample is selected from the group consisting of (i) presence or absence of an abnormality in the urine sample, (ii) presence or absence of a suspicion of pathological proteinuria, (iii) presence or absence of a suspicion of tubular proteinuria, (iv) presence or absence of a suspicion of glomerular proteinuria, and (v) any combination of (i) to (iv).

[11] The method according to any one of [1] to [10], wherein the protein detection reagent for detecting protein in the urine sample and the detection reagent having a higher detection sensitivity to albumin than the protein detection reagent are arranged in an analysis tool, or are dissolved in a liquid to form liquid reagents.

[12] An analyzer including:
a measurement portion configured to optically analyze coloration after a urine sample is brought into contact with two types of detection reagents that differ in reactivity to at least one urinary protein;
a recording portion configured to record data for evaluating the urine sample;
an operation portion configured to calculate an indicator from results of the optical analysis of the two types of detection reagents, and configured to evaluate the urine sample based on the data for evaluating the urine sample; and
an output portion configured to output data after the evaluation.

[13] An analyzer including:
a measurement portion configured to optically analyze coloration after a urine sample is brought into contact with two types of detection reagents that differ in their relative reactivities to a urinary protein a and a urinary protein b;
a recording portion configured to record data for evaluating the urine sample;
an operation portion configured to calculate an indicator from results of the optical analysis of the two types of detection reagents, and configured to evaluate the urine sample based on the data for evaluating the urine sample; and
an output portion configured to output data after the evaluation.

[14] An analyzer including:
a measurement portion configured to optically analyze coloration after a urine sample is brought into contact with a protein detection reagent for detecting protein in the urine sample, and coloration after the urine sample is brought into contact with a detection reagent having a higher detection sensitivity to albumin than the protein detection reagent;
a recording portion configured to record data for evaluating the urine sample;
an operation portion configured to calculate an indicator from results of the optical analysis of the two types of detection reagents, and configured to evaluate the urine sample based on the data for evaluating the urine sample; and
an output portion configured to output data after the evaluation.

[15] The analyzer according to any one of [12] to [14], wherein the data for evaluating the urine sample includes information that associates the indicator with the evaluation selected from the group consisting of (i) presence or absence of an abnormality in the urine sample, (ii) presence or absence of a suspicion of pathological proteinuria, (iii) presence or absence of a suspicion of tubular proteinuria, (iv) presence or absence of a suspicion of glomerular proteinuria, and (v) any combination of (i) to (iv).

[16] An analyzer configured to perform the method for evaluating a urine sample according to any one of [1] to [11].

[17] An analysis system including:
an analysis tool; and
an analyzer that uses the analysis tool for an analysis,
the analysis tool including two types of detection reagents that differ in reactivity to at least one urinary protein or two types of detection reagents that differ in their relative reactivities to a urinary protein a and a urinary protein b,
the analyzer including:
a measurement portion configured to optically analyze coloration after a urine sample is brought into contact with the two types of detection reagents;
a recording portion configured to record data for evaluating the urine sample;
an operation portion configured to calculate an indicator from results of the optical analysis of the two types of detection reagents, and configured to evaluate the urine sample based on the data for evaluating the urine sample; and
an output portion configured to output data after the evaluation.

[18] The analysis system according to [17], wherein a combination of the two types of detection reagents is a combination of a protein detection reagent for detecting protein in the urine sample and a detection reagent having a higher detection sensitivity to albumin than the protein detection reagent.

[19] The analysis system according to [17] or [18], including the analyzer according to any one of [12] to [16].

Hereinafter, the present disclosure will be described in more detail by way of examples. However, the present disclosure is not limited to the following examples.

EXAMPLES

Experimental Example 1

Confirmation of Difference in Relative Reactivities to Urinary Proteins

The following pseudo-proteinuria samples were prepared. With respect to each of the urinary proteins in the pseudo-proteinuria samples, the reactivity of the urinary protein with a protein test pad and the reactivity of the urinary protein with an albumin test pad were compared to confirm a difference in the relative reactivities to the urinary proteins. The protein test pad and the albumin test pad were arranged in a urinalysis test strip.

[Pseudo-Proteinuria Sample]

Pseudo-proteinuria samples were prepared by adding any one of the urinary proteins including albumin, transferrin, α1-microglobulin, β2-microglobulin, and Tamm-Horsfall glycoprotein (see Table 4) at a final concentration of 20 mg/dL to urinary protein-negative urine. In this case, albumin and transferrin are the main proteins in glomerular proteinuria, α1-microglobulin and β2-microglobulin are the proteins in tubular proteinuria, and Tamm-Horsfall glycoprotein causes urinary casts.

TABLE 4

| Urinary protein added to urinary protein-negative urine (final concentration 20 mg/dL) | Explanation |
|---|---|
| Albumin | Proteins in glomerular proteinuria |
| Transferrin | |
| α1-microglobulin | Proteins in tubular proteinuria |
| β2-microglobulin | |
| Tamm-Horsfall glycoprotein | Protein causing urinary cast |

[Urinalysis Test Strip and Sample Analyzer]

The urinalysis test strip was a test strip (trade name: Uriflet S 10HB, manufactured by ARKRAY, Inc.) that includes an albumin test pad (i.e., a test pad for detecting trace albumin or trace protein in urine), a protein test pad (i.e., a test pad for detecting total protein in a urine sample), and a creatinine test pad. The principle of the albumin test pad is a dye-binding method (4,5,6,7-tetrachloro-2',4',5',7'-tetraiodo-fluorescein disodium salt). The principle of the protein test pad is a protein error method (tetrabromophenol blue). A reflectance measuring apparatus was used as a sample analyzer for measuring the above urinalysis test strip. In the reflectance measuring apparatus, reflectance (%) was output as the results of the measurement.

In many cases, the protein test pad generally uses the protein error method. In the albumin test pad, the reactivity of the albumin is changed by adjusting the formulation of the reagent of the protein test pad, so that the detection sensitivity to albumin is increased.

[Result]

The pseudo-proteinuria samples were analyzed by using the two types of test strips and the sample analyzer. The reactivity value of each of the urinary proteins relative to albumin was determined for each of the test strips. Next, the reactivity value of each of the urinary proteins relative to albumin was compared between the albumin test pad (A test pad) and the protein test pad (P test pad). Table 5 shows the results.

TABLE 5

| Urinary protein | Relative reactivity value with respect to albumin | Difference in relative reactivity value A test pad/P test pad |
|---|---|---|
| Transferrin | A test pad > P test pad | 1.08 |
| α1-microglobulin | A test pad < P test pad | 0.87 |
| β2-microglobulin | A test pad < P test pad | 0.80 |
| Tamm-Horsfall glycoprotein | A test pad < P test pad | 0.35 |

As shown in Table 5, the reactivity of transferrin relative to albumin was higher with the albumin test pad (A test pad) than with the protein test pad (P test pad). On the other hand, the reactivity of α1-microglobulin, β2-microglobulin, and Tamm-Horsfall glycoprotein relative to albumin was higher with the protein test pad (P test pad) than with the albumin test pad (A test pad). Thus, Table 5 shows that the reactivity of each of the urinary proteins relative to albumin was different between the two types of test pads (i.e., the albumin test pad and the protein test pad). In particular, such a difference was large for α1-microglobulin, β2-microglobulin, and Tamm-Horsfall glycoprotein.

[Simulation of Indicator (A/P Value) by Pseudo-Proteinuria Sample]

The indicator (A/P value) was calculated based on the measured data using the pseudo-proteinuria samples.

[Calculation Method of A/P Value]

The indicator (A/P value) is a ratio of the analysis data (A value) of the albumin test pad to the analysis data (P value) of the protein test pad, and is calculated by the following formula. In other words, the A/P value is obtained by dividing the A/C value by the P/C value.

$$A/P \text{ value} = [A/C \text{ value}]/[P/C \text{ value}]$$

[Calculation Method of A/C Value and P/C Value]

The A/C value indicates that the analysis data (A value) of the albumin test pad is corrected with the analysis data (C value) of the creatinine test pad. The P/C value indicates that the analysis data (P value) of the protein test pad is corrected with the analysis data (C value) of the creatinine test pad. For example, the A/C value and the P/C value are calculated by the following formulas.

$$A/C \text{ value} = (100 - \text{reflectance of albumin test pad})/\text{reflectance of creatinine test pad}$$

$$P/C \text{ value} = (100 - \text{reflectance of protein test pad})/\text{reflectance of creatinine test pad}$$

The A/P values were calculated using the data obtained by the analysis of the pseudo-proteinuria samples with the two types of test strips and the sample analyzer. The resultant A/P values were as follows: 0.41 for no protein added; 1.26 for albumin; 1.13 for transferrin; 1.04 for β2-microglobulin; 0.75 for α1-microglobulin; and 0.44 for Tamm-Horsfall glycoprotein. Table 6 and FIG. 6 show the results.

TABLE 6

| | Urinary protein contained in pseudo-proteinuria sample | P/C | A/C | A/P |
|---|---|---|---|---|
| | No protein added | 0.67 | 0.28 | 0.41 |
| Urinary proteins in glomerular proteinuria | Albumin | 1.11 | 1.39 | 1.26 |
| | Transferrin | 0.97 | 1.10 | 1.13 |
| Urinary proteins in tubular proteinuria | α1-microglobulin | 0.82 | 0.62 | 0.75 |
| | β2-microglobulin | 1.09 | 1.13 | 1.04 |
| Urinary protein causing urinary cast | Tamm-Horsfall glycoprotein | 0.76 | 0.34 | 0.44 |

As shown in Table 6 and FIG. 6, the A/P values were increased in the following order: the sample to which no protein was added<the sample to which the urinary protein causing urinary cast was added<the sample to which the urinary proteins in tubular proteinuria were added<the sample to which the urinary proteins in glomerular proteinuria were added. There was a difference in the A/P value between the sample to which no protein was added and the samples to which the urinary proteins in tubular proteinuria were added. Moreover, there was a difference in the A/P value between the sample to which no protein was added and the samples to which the urinary proteins in glomerular proteinuria were added. Further, there was a difference in the A/P value between the samples to which the urinary proteins in tubular proteinuria were added and the samples to which the urinary proteins in glomerular proteinuria were added. Thus, the results showed that the A/P value could be the indicator that gives information about a suspicion of tubular proteinuria and/or glomerular proteinuria.

Experimental Example 2

Quantification of Clinical Urine Sample

In order to confirm the effectiveness of the indicator (A/P value), clinical evaluation data of 79 urine samples was used. First, the following four urinary proteins and creatinine in the 79 urine samples were quantified (i.e., with higher accuracy than the test strip) under the following conditions. Then, the urine samples were classified into A to D groups under the following conditions.

[Quantitative Method]
1) Albumin
Reagent name: Microalbumin-HA test
Principle/Maker: Immunonephelometry/Wako Pure Chemical Industries, Ltd.
2) Total protein
Reagent name: Micro TP-AR (manufactured by Wako Pure Chemical Industries, Ltd.)
Principle/Maker: PR-Mo method/Wako Pure Chemical Industries, Ltd.
3) α1-microglobulin
Reagent name: Superior ALPHA-I
Principle/Maker: Immunonephelometry/Iatron, Inc.
4) β2-microglobulin
Reagent name; Superior BMG-II
Principle/Maker: Immunonephelometry/Iatron, Inc.
5) Creatinine
Reagent name: Master test CRE
Principle/Maker: Enzymic method/ARKRAY, Inc.

[Classification Method]

The values of albumin (A/C value), α1-microglobulin (α1-m/C value), and β2-microglobulin (β2-m value) were obtained from the above quantitative method, and determined as negative (−) or positive (+) according to the following criteria. Then, the samples were classified into A to D groups based on the results of the quantification and Table 7. "A/C" indicates that the albumin value is corrected with creatinine, and the same is true for "α1-m/C". In Table 7, the section of "α1-m/C or β2-m" shows "+" if any one of them is positive, and shows "−" if both of them are negative.

[Criteria for Determining Positive/Negative]

The values of albumin (A/C), α1-microglobulin (α1-m/C), and β2-microglobulin (β2-m) were determined as positive (+) if they were more than the following cut off values, and determined as negative (−) if they were not more than the following cut off values, respectively. The cut off values are only examples and not limited to the following values.

[Cut Off Value]
A/C: 30 mg/g CRE
α1-m/C: 14 mg/g CRE
β2-m: 0.25 mg/L

TABLE 7

| | Result of quantification | | |
|---|---|---|---|
| | A/C | α1-m/C or β2-m | Evaluation |
| A group | − | − | Group in which no abnormality was found. |
| B group | − | + | Group in which there was a suspicion of tubular proteinuria. |
| C group | + | + | Group in which there was a suspicion of both tubular proteinuria and glomerular proteinuria. |
| D group | + | − | Group in which there was a suspicion of glomerular proteinuria. |

[Result of Quantitative Classification]

As a result of the classification of the 79 urine samples into A to D groups based on the quantification, the A group included 21 samples, the B group included 12 samples, the C group included 26 samples, and D group included 20 samples. Using these samples, the effectiveness of the indicator (A/P value) was confirmed in the following manner.

Experimental Example 3

Confirmation 1 of Effectiveness of Indicator (A/P Value)

The 79 samples of Experimental Example 2 were analyzed by using the test strip including an albumin test pad, a protein test pad, and a creatinine test pad, and the A/C value and the P/C value were calculated. Next, the 79 samples were classified into the first to fourth groups based on negative (−) and positive (+) of the A/C value and the P/C value for each item, as shown in Table 8. The A/C value measured by the test strip was determined as negative (−) if it was less than 30 mg/g CRE, and determined as positive (+) if it was not less than 30 mg/g CRE. The P/C value measured by the test strip was determined as negative (−) if it was less than 80 mg/g CRE, and determined as positive (+) if it was not less than 80 mg/g CRE. The measurement of the A/C value and the P/C value was performed by using the test strip (with the same formulation as that of Uriflet S 10HB described above) including the test items of protein, albumin, and creatinine. The sample analyzer using the test strip was AUTION MAX AX-4280 (trade name, manufactured by ARKRAY, Inc.).

TABLE 8

| Group | A/C | P/C | Number of samples | |
|---|---|---|---|---|
| 1 | − | − | 42 | Negative: No abnormality was found. |
| 2 | − | + | 2 | Positive: An abnormality was found, and there was a suspicion of renal proteinuria. |
| 3 | + | − | 6 | |
| 4 | + | + | 29 | |

As shown in Table 8, 42 samples were classified as negative (the first group) based on the A/C value and the P/C value of the test strip.

Next, the A/P value was calculated from the results of the analysis of the A/C value and the P/C value, and the 42 samples of the first group (without abnormality) in Table 8 were classified again based on the following data for evaluation (i.e., the criteria and evaluation using the A/P value). Consequently, the group without abnormality included 20 samples, and the group with abnormality included 22 samples (see Table 9). Moreover, the 20 samples of the group without abnormality and the 22 samples of the group with abnormality, which had been classified by the A/P value, were classified again into the A group (without abnormality) and the B to D groups (with abnormality) based on the quantification of Experimental Example 2, as shown in Table 7. Table 9 shows the results.

[Criteria and Evaluation Using A/P Value]

If A/P<0.83, the sample is classified as negative (without abnormality).

If A/P≥0.83, the sample is classified as positive (with abnormality). The data for evaluation (i.e., the threshold value) using the A/P value was prepared and set by using the results of the quantitative classification of Experimental Example 2. More specifically, the threshold value was −2.5% of the median of the A/P values ([the median of the A/P values]−[the median of the A/P values]*0.25) of the 12 samples of the B group in Table 7.

TABLE 9

|  | Classification by A/P | Quantitative classification | |
|---|---|---|---|
|  |  | B to D groups with abnormality | A group without abnormality |
| Negative: No abnormality was found. | 20 | 5 | 15 |
| Positive: An abnormality was found. | 22 | 16 | 6 |

As shown in Table 9, when the 42 samples classified by the A/P value were further classified based on the quantification, 5 samples out of the 20 samples that had been classified into the group without abnormality had an abnormal quantitative value. On the other hand, 16 samples out of the 22 samples that had been classified into the group with abnormality had an abnormal quantitative value. Thus, 21 (5+16) abnormal samples were undetectable only by using the A/C value and the P/C value of the test strip. However, Table 9 shows that the use of the A/P value extracted the 16 abnormal samples and reduced the number of undetected abnormal samples.

Experimental Example 4

Confirmation 2 of Effectiveness of Indicator (A/P Value)

The 79 samples that were analyzed by using the test strip including the albumin test pad, the protein test pad, and the creatinine test pad in Experimental Example 3 were then classified into the first to fourth groups based on the following data for evaluation using the A/P value of the test strip (i.e., the criteria and evaluation using the A/P value), as shown in Table 10. Consequently, the first group included 27 samples, the second group included 20 samples, the third group included 7 samples, and the fourth group included 25 samples (see Table 10).

TABLE 10

|  | Criteria | Evaluation | Number of samples |
|---|---|---|---|
| First group | A/P < 0.83 | Group in which no abnormality was found. | 27 |
| Second group | 0.83 ≤ A/P < 0.88 | Group in which there was a suspicion of tubular proteinuria. | 20 |
| Third group | 0.88 ≤ A/P < 0.91 | Group in which there was a suspicion of both tubular proteinuria and glomerular proteinuria. | 7 |
| Fourth group | 0.91 ≤ A/P | Group in which there was a suspicion of glomerular proteinuria. | 25 |

The criteria of the data for evaluation using the A/P value were prepared and set by using the results of the quantitative classification of Experimental Example 2.

The rates of agreement between the first to fourth groups according to the classification based on the A/P value of the test strip and the A to D groups according to the classification based on the quantification were examined. Table 11 shows the results.

TABLE 11

|  |  | Quantitative test | | | | | |
|---|---|---|---|---|---|---|---|
|  |  | A group | B group | C group | D group | Total number of samples | Rate of agreement |
| A/P | First group | 15 | 4 | 6 | 2 | 27 | 56% |
|  | Second group | 5 | 7 | 6 | 2 | 20 | 35% (65%) |
|  | Third group | 1 | 0 | 3 | 3 | 7 | 43% |
|  | Fourth group | 0 | 1 | 11 | 13 | 25 | 52% |
|  | Total | 21 | 12 | 26 | 20 | 79 |  |

As shown in Table 11, the rate of perfect agreement between the first group and the A group in which no abnormality was found was 56% (15/27). The rate of perfect agreement between the second group and the B group in which there was a suspicion of tubular proteinuria alone was 35% (7/20). In this case, when the B group was combined with the C group in which there was a suspicion of both tubular proteinuria and glomerular proteinuria, the rate of perfect agreement was 65% ((7+6)/20). The rate of perfect agreement between the third group and the C group in which there was a suspicion of both tubular proteinuria and glomerular proteinuria was 43% (3/7). The rate of perfect agreement between the fourth group and the D group in which there was a suspicion of glomerular proteinuria alone was 52% (13/25). Thus, Table 11 shows that the introduction of the A/P value extracted the abnormal samples, and was also able to determine whether there was a suspicion of tubular proteinuria, whether there was a suspicion of glomerular proteinuria, or whether there was a suspicion of both tubular proteinuria and glomerular proteinuria.

Experimental Example 5

Confirmation 3 of Effectiveness of Indicator (A/P Value)

The 20 samples of the second group in Table 10 were further studied and evaluated by using the A/C value as an indicator in addition to the A/P value. In other words, the 20 samples of the second group were classified into three groups based on the following data for evaluation using the A/P value and the A/C value (i.e., the criteria and evaluation using the A/P value and the A/C value). Table 12 shows the results.

TABLE 12

|  | Criteria | Evaluation | Number of samples |
|---|---|---|---|
| 2-1 group | 0.83 ≤ A/P < 0.88 and A/C < 0.53 | Group in which no abnormality was found. | 4 |
| 2-2 group | 0.83 ≤ A/P < 0.88 and 0.53 ≤ A/C < 0.64 | Group in which there was a suspicion of tubular proteinuria. | 8 |
| 2-3 group | 0.83 ≤ A/P < 0.88 and 0.64 ≤ A/C | Group in which there was a suspicion of both tubular proteinuria and glomerular proteinuria. | 8 |

The rates of agreement between the 2-1 to 2-3 groups according to the classification based on the A/P value and the A/C value of the test strip and the A to D groups according to the classification based on the quantification were examined.

Table 13 shows the results.

TABLE 13

|  |  | Quantitative test | | | | | |
|---|---|---|---|---|---|---|---|
|  |  | A group | B group | C group | D group | Total number of samples | Rate of agreement |
| A/P and A/C | 2-1 group | 4 | 0 | 0 | 0 | 4 | 100% |
|  | 2-2 group | 1 | 7 | 0 | 0 | 8 | 88% |
|  | 2-3 group | 0 | 0 | 6 | 2 | 8 | 75% |
|  | Total | 5 | 7 | 6 | 2 | 20 |  |

As shown in Table 13, the rate of perfect agreement between the 2-1 group and the A group in which no abnormality was found was 100% (4/4). The rate of perfect agreement between the 2-2 group and the B group in which there was a suspicion of tubular proteinuria alone was 88% (7/8). The rate of perfect agreement between the 2-3 group and the C group in which there was a suspicion of both tubular proteinuria and glomerular proteinuria was 75% (6/8). Thus, since the conditions of the A/C value were added to the preparation of the data for evaluation using the A/P value, more accurate information about proteinuria and/or nephropathy was provided. It has been difficult to classify urine as tubular proteinuria if proteins present in the urine are not separated and fractionated individually. However, as described above, the information about proteinuria, particularly the information about tubular proteinuria can be accurately provided in a simple manner. In this example, the second group was evaluated by using the A/C value as an indicator. However, the present disclosure is not limited thereto, and may use the A/C value as an indicator to evaluate, e.g., the third group.

In the examples, the data for evaluation (i.e., the threshold value) using the A/P value is only an embodiment, and may be modified in accordance with the formulation of the reagent, the accuracy required for the output results, the purpose, or the like. In the examples, the A/P value was used for the analysis, but the P/A value can also be used. Moreover, in the examples, the albumin test pad (A test pad) and the protein test pad (P test pad) were used, but other test strips can also be used. Due to a difference in reactivity between two or more test strips, the results of the measurement with the test strips are combined and calculated to produce an indicator, and the evaluation can be performed based on the indicator. Further, in the examples, the test strips (dry type) were used, but a liquid reagent can also be used.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method for evaluating a urine sample for the presence of tubular proteinuria based on an indicator calculated from a P value and an A value, the method comprising:

detecting the presence of protein in the urine sample by contacting the sample with a reagent pad comprising a protein detection agent, where the P value reflects the protein in the sample; and detecting the presence of albumin in the urine sample by contacting the sample with a reagent pad comprising an albumin detection reagent, the albumin detection reagent having a higher detection sensitivity to albumin than the protein detection reagent where the A value reflects the albumin in the sample;

wherein the indicator comprises the following A/P value or P/A value:

$$A/P \text{ value} = [A \text{ value}]/[P \text{ value}] \text{ or } [A/C \text{ value}]/[P/C \text{ value}];$$

$$P/A \text{ value} = [P \text{ value}]/[A \text{ value}] \text{ or } [P/C \text{ value}]/[A/C \text{ value}],$$

where C is a value that reflects creatinine present in the urine sample and is determined by contacting the sample with a creatinine detection reagent, and where C corrects the A value and the P value;

comparing the indicator to a threshold value, and determining the presence of tubular proteinuria in the urine sample if the indicator is greater than or equal to the threshold value.

2. The method according to claim 1, wherein the indicator further comprises the A/C value.

3. The method according claim 1, further comprising evaluating (i) presence of an abnormality in the urine sample, (ii) presence of pathological proteinuria, (iii) presence of glomerular proteinuria, or (iv) any combination of (i) to (iii).

4. The method according to claim 1, wherein the protein detection reagent and the albumin detection reagent are present in an analysis tool.

5. The method according to claim 1, further comprising bringing the urine sample into contact with a test strip comprising the reagent pads.

6. An analysis system comprising:

an analysis tool; and an analyzer comprising the analysis tool, where the analysis tool comprises a reagent pad comprising a protein detection agent and a reagent pad comprising an albumin detection agent, wherein the albumin detection agent has a higher detection sensitivity to albumin than the protein detection agent, and where the analyzer comprises:

a measurement portion configured to optically analyze coloration after a urine sample is brought into contact with the protein detection reagent and the albumin detection reagent;

a recording portion configured to record coloration data for evaluating the urine sample;

an operation portion configured to calculate a P value using the protein detection reagent and an A value using the albumin detection reagent and configured to calculate an indicator from optical analysis results of the protein detection reagent and the albumin detection reagent, and configured to evaluate presence of tubular proteinuria in the urine sample based on A value and P value data; and an output portion configured to output A value and the P value data after the evaluation, wherein the indicator comprises the following A/P value or P/A value:

$$A/P \text{ value} = [A \text{ value}]/[P \text{ value}] \text{ or } [A/C \text{ value}]/[P/C \text{ value}];$$

$P/A \text{ value}=[P \text{ value}]/[A \text{ value}] \text{ or } [P/C \text{ value}]/[A/C \text{ value}]$, where C is a value that reflects creatinine present in the urine sample and corrects the A value and the P value, and wherein the operation portion compares the indicator to a threshold value and determines the presence of tubular proteinuria in the urine sample if the indicator is greater than or equal to the threshold value.

7. The analysis system according to claim 6, the indicator further comprises the A/C value.

8. The analysis system according to claim 6, wherein the operation portion is further configured to evaluate (i) presence of an abnormality in the urine sample, (ii) presence of pathological proteinuria, (iii) presence of glomerular proteinuria, or (iv) any combination of (i) to (iii).

* * * * *